United States Patent [19]

Majerus et al.

[11] Patent Number: 4,912,207
[45] Date of Patent: Mar. 27, 1990

[54] DNA CLONE OF HUMAN THROMBOMODULIN AND PORTIONS THEREOF

[75] Inventors: Philip W. Majerus; J. Evan Sadler, both of St. Louis, Mo.

[73] Assignee: Washington University, St. Louis, Mo.

[21] Appl. No.: 47,246

[22] Filed: May 6, 1987

[51] Int. Cl.$^4$ ...................... C07H 21/00; C07H 21/04
[52] U.S. Cl. ........................................ 536/27; 536/28; 536/29
[58] Field of Search .................................... 536/27–29

[56] References Cited

PUBLICATIONS

Esmon et al., J. Biol. Chem. 257, 859–864 (1982).
Suzuki et al., Biochim. Biophys. Acta 882, 343–352 (1986).
Jakubowski et al., J. Biol. Chem. 261, 3876–3882 (1986).
Maruyama et al., J. Clin. Invest. 75, 987–991 (1985).
Salem et al., J. Biol. Chem. 259, 12246–12451 (1984).
Maruyama et al., J. Cell. Biol. 101, 363–371 (1985).
Jackman et al., Proc. Natl. Acad. Sci. USA, 83, 8834–8838 (1986).
Maruyama and Majerus, J. Biol. Chem. 260, 15432–15438 (1985).
Bourin et al., Proc. Natl. Acad. Sci. USA 83, 5924–5928 (1986).
Freyssinet et al., Thromb. Haemost. 55, 112–118 (1986).
Esmon, Science 235, 1348–1352 (1987).
Suzuki et al., EMBo Journal, vol. 6, pp. 1891–1897, 1987.

Primary Examiner—Johnnie R. Brown
Assistant Examiner—L. Eric Crane
Attorney, Agent, or Firm—Scott J. Meyer; James W. Williams, Jr.

[57] ABSTRACT

A cDNA having a base sequence for human thrombomodulin has been cloned and characterized and the amino acid sequence of the human thrombomodulin has been determined.

6 Claims, 11 Drawing Sheets

FIG. 3A.

| 3A | 3B |
|---|---|
| 3C | 3D |
| 3E | 3F |

FIGURE PLAN

```
GGCAGCGCGCAGGGCAAGAAGTGTCTGGGCTGGGACGGACAGGAGAGGCTGTCGCCAT

CGCCTGCACGGGCCCTGGGTAACATGCTTGGGGTCCTGGTCCTTGGCGCTGGCGCTGGCC
                  M  L  G  V  L  V  L  G  A  L  A

GAGCACGACTGCTTCGCGCTCTACCCGGGCCCCGACCTTCCTCAATGCCAGTCAGATC
 E  H  D  C  F  A  L  Y  P  G  P  A  T  F  L  N  A  S  Q  I

TCCTTGCTACTGAACGGCGACGGCGTTGGCGCGGGCGCCCTCGATCGGCTGCAG
 S  L  L  L  N  G  D  G  G  V  G  R  R  R  L  W  I  G  L  Q

ACGGGAGACAACAACACCAGCTATAGCAGGTGGGCACGGCTCGACCTCAATGGGCTCCC
 T  G  D  N  N  T  S  Y  S  R  W  A  R  L  D  L  N  G  A  P
                                      T-MI-R3

ATCTGGAGGAGCAGCAGTGCGAAGTGAAGGCCGATGGCTTCCTCTGCGAGTTCCACTTC
 I  W  E  E  Q  Q  C  E  V  K  A  D  G  F  L  C  E  F  H  F

ACCTACGGCACCCCGTTCGCGGCCCGGGAGCGGACTTCCAGGCGCTGCCGGTGGGCAGC
 T  Y  G  T  P  F  A  A  R  G  A  D  F  Q  A  L  P  V  G  S

CAGGGGCACTGGGCCAGGAGGCGCCGGGCGCTTGGGACTGCAGCGTGGAGAACGGCGGC
 Q  G  H  W  A  R  E  A  P  G  A  W  D  C  S  V  E  N  G  G
           T-MI-R1                          1

GCCCTGCAGGCAGACGGGCGCTCTGCACCGCTACCCGGACAGTCCTGCAACGACCTC
 A  L  Q  A  D  G  R  S  C  T  A  S  A  T  Q  S  C  N  D  L
                                              2

ACCGGCTACCGGCTGGCCGCGGCCGACCAACACCGGTGCGAGGACGTGGATGACTGCATACTG
 T  G  Y  R  L  A  A  D  Q  H  R  C  E  D  V  D  D  C  I  L
                            T-MI-R2         3
```

FIG. 3B.

```
CGGCGTCCTGTGCCCCTCTGCTCCGGCACGGCCCTGTCGCAGTGCCGCGCTTTCCCCGG                                    119

CTGGCCGGCCTGGGGTTCCCCGCACCCGCAGAGCCGGCAGCCAGTGCAGCCAGTGCGTC                                    241
 L  A  G  L  G  F  P  A  P  A  E  P  Q  P  G  G  S  Q  C  V                                    31

TGCGACGGACTGCGGGGCCACCTAATGACAGTGCGCTCCTCGGTGGCTGCCGATGTCATT                                   361
 C  D  G  L  R  G  H  L  M  T  V  R  S  S  V  A  A  D  V  I                                    71

CTGCCACCCGGCTGCGGGGACCCCAAGCGCCTCGGGCCCCTGCGCGGCTTCCAGTGGGTT                                   481
 L  P  P  G  C  G  D  P  K  R  L  G  P  L  R  G  F  Q  W  V                                    111

CTCTGCGGCCCGTTGTGCGTCGCTGTCTCCGCGTGGAGCCACTGTGCCCAGCGAGCCG                                     601
 L  C  G  P  L  C  V  A  V  S  A  A  E  A  T  V  P  S  E  P                                    151

CCAGCCACCTGCAGGCCACTGGCTGTGGAGCCCGGCGCCGGAGCCCGTCTCGATC                                        721
 P  A  T  C  R  P  L  A  V  E  P  G  A  A  A  A  V  S  I                                       191

TCCGCCGCGGTGGCTCCCCTCGGCTTACAGTAATGTGCACCGCCACCGGAGCGGTC                                       841
 S  A  A  V  A  P  L  G  L  Q  L  M  C  T  A  P  P  G  A  V                                    231

TGCGAGCACGGCGTGCAATGCGATCCCCTGGGGCTCCCCGGCCAGCGCGGCCAGCCGGGCC                                  961
 C  E  H  A  C  N  A  I  P  G  A  P  R  C  Q  C  P  A  G  A                                    271
                                    T-MO-RI

TGCGAGCACTTCTGCGTTCCCAACCCGGACCAGCCGGGCTCCTACTCGTCGTGCATGTGCGAG                                1081
 C  E  H  F  C  V  P  N  P  D  Q  P  G  S  Y  S  C  M  C  E                                    311

GAGCCCAGTCCGTGTCCGCAGCGCTGTGTCAACACAGGGTGGCTTCGAGTGCCACTGC                                     1201
 E  P  S  P  C  P  Q  R  C  V  N  T  Q  G  G  F  E  C  H  C                                    351
```

FIG. 3C.

```
TACCCTAACTACGACCTGGTGGACGGGCGAGTGTGTGGAGCCCGTGCTTCAGA
 Y  P  N  Y  D  L  V  D  G  E  C  V  E  P  V  D  P  C  F  R
                                               4
GAGGGCTTCGCGCCCATTCCCCACGAGCCGCACAGGTGCAACAGGTTTTGCAACCAGACT
 E  G  F  A  P  I  P  H  E  P  H  R  C  Q  M  F  C  N  Q  T
           ‾‾‾‾‾‾‾‾‾‾‾‾‾‾‾‾‾‾‾‾‾‾‾‾‾‾‾‾‾‾‾‾‾‾‾‾‾‾5
ATCCTGGACGACGGTTTCATCTGCACGGACATCGACGAGTGCGAAAACGGGGGCTTCTGC
 I  L  D  D  G  F  I  C  T  D  I  D  E  C  E  N  G  G  F  C
                                      6
CTTGCCCGCCACATTGGCACGGACTGTGACTCCGGCAAGGTGGACGGTGGCGACAGCGGC
 L  A  R  H  I  G  T  D  C  D  S  G  K  V  D  G  G  D  S  G

CTCGTGCATTCGGGCTTGCTCTCATAGGCATCTCCATCGCGAGCCTGTGCCTGGTGGCCG
 L  V  H  S  G  L  L  I  G  I  S  I  A  S  L  C  L  V  V  A

TACAAGTGCGCGGCCCCTTCCAAGGAGGTAGTGCTGCAGCACGTGCGAGCGAGCGGACG
 Y  K  C  A  A  P  S  K  E  V  V  L  Q  H  V  R  T  E  R  T

CCTCACCCCCAGCTTTGCTACCAAAGCACCTTAGCTGCATTACAGCTGGAGAAGACCCT

AGGGAGGAGAATGAGCCTCGGCCTCTTCCGTGACGTCACTGGACCACTGGCAATGATGG

AGGGTGAGCGTTATTGGTCGGCAGCCTTGGGCAGACCTTGACCTCGTGGGCTAGGGAT

TGTATGTCTCCAGTATCCACTTTGCACAGCTCTCCGGTCTCTCTCTCTCTACAAACTCCC
```

FIG. 3D.

```
GCCAACTGCGAGTACCAGTGCCAGCCCCTGAACCAAACTAGTACCTCTGCGTCTGCGCC    1321
 A  N  C  E  Y  Q  C  Q  P  L  N  Q  T  S  Y  L  C  V  C  A     391
 T-RI                          •
GCCTGTCCAGCCGACTGCGACCCCAACACCCAGGCTAGTGCCCTGAAGTGCCCTGAAGGCTAC 1441
 A  C  P  A  D  C  D  P  N  T  Q  A  S  C  E  C  P  E  G  Y     431
TCCGGGGGTGTGCCACAACCTCCCCGGTACCTTCGAGTGCATCTGCGGGCCGACTCGGC    1561
 S  G  V  C  H  N  L  P  G  T  F  E  C  I  C  G  P  D  S  A     471
TCTGGGAGCCCCCCGAGCCCCAGCCCCGGCTCCACCTTGACTCCTCCGGCCGTGGGG      1681
 S  G  E  P  P  P  S  P  T  P  G  S  T  L  T  P  P  A  V  G     511
CTTTTGGCGCTCCTCTGCCACTGCGCAAGAAGCAGGGCGCCGCCAGGGCCAAGATGGAG    1801
 L  L  A  L  L  C  H  L  R  K  K  Q  G  A  A  R  A  K  M  E     551
CCGCAGAGACTCTGAGGCGGCCTCCGTCCAGGAGCCTGGCTCCGTCCAGGAGCCTGTGCCT  1921
 P  Q  R  L  ★                                                   575
CCCCGCACCCCCAAGCTGTTTCTTCTATTCCATGGCTAACTGGCGAGGGGTGATTAG     2041
CAATTTTGTAACGAAGACACAGACTGCGATTTGTCCCAGGTCCTCACTACGGGCGCAGG   2161
GACTAAAAATATTTATTTTTTAAGTATTTAGGTTTTTGTTTTGTTTCCTTTGTTCTTACC  2281
ACTTGTCATGTGACAGGTAAAACTATCTTGGTGAATTTTTTTTCCTAGCCCTCTCACATT  2401
```

```
TATGAAGCAAGCCCCACTTATTCCCCATTCTTCCTAGTTTTCTCCTCCCAGGAACTGGGC
CTCAGACAGAACCCCTACATGAAACAGAAACAAAAACACTAAAAATAAAAATGGCCATTT
TTAAACAAAGGTTGAGATGTAAAAGGTATTAAATTGATGTTGCTGGACTGTCATAGAAAT
TTGATTTGTACTGAAAAATGGTAATTGTGCTAATCTTCTTATGCAATTTCCTTTTTGT
AGAGACAAACACCTCCCAGGAGACAGTTCAAGAAAGCTTCAAACTGCATGATTCATGCCA
TGGTCTCTGTGGAATTGGGAGCTTGGGAATGGATCCTGGAGGATGCCCAATTAGGGCTAG
CTGAACAAGAATTGGAAGCTGCCCTGCCCATGGGAGCTGGTTAGAAATGCAGAATCCTAG
GCTCAGTAATTTGAGGACAACCATTCCAGACTGCTTCCAATTTCTGGAATACATGAAAT
TTCTTTGTGTAGCTTTGCTCTTTGGTAGAAAAGGCTAGGTACACAGCTCTAGACACTGCC
ATGGAAATAAATGTATGATAGAAATGTAACTTTTGTAAGACAAAGGTTTTCCTCTTCTAT
GGCAAAATCCTTGCTTATGACATCACTTGTACAAAATAAACAAATAACAATGTGAAAAAA
```

FIG. 3E.

```
CAACTCACCTGAGTCACCTGCCTGACCCTACTTCTTTTGCTCTCTTAGCTGTCTG      2521
GCTTTTTCACCAGATTTGCTAATTTATCCTGAAATTTCAGATTCCCAGAGCAAAATAATT  2641
TACACCCAAAGAGGTATTTATCTTTACTTTTAAACAGTGAGCCTGAATTTTGTTGCTGTT  2761
TATTATTACTTATTTTTGACAGTGTTGAAAATGTTCAGAAGGTTGCTCTAGATTGAGAGA  2881
ATTAGCAATTGACTGTCACTGTTCCTTGTCACTGGTAGACCAAAATAAAACCAGCTCTAC  3001
CCTTAATCAGGTCCTCAGAGAATTTCTACCATTTCAGAGAGGCCTTTTGGAATGTGGCCC  3121
GCTCCACCCCATCCAGTTCATGAGAATCTATATTTAACAAGATCTGCAGGGGGTGTGTCT  3241
ATAGATCAGTTATAAGTAGCAGGCCAAGTCAGGCCCTTATTTTCAAGAAACTGAGGAATT  3361
ACACAGGGTCTGCAAGGTCTTTGGTTCAGCTAAGCTAGGAATGAAATCCTGCTTCAGTGT  3481
TTTGTAAACTCAAAATATTTGTACATAGTTATTTATTTATTTATTGGAGATAATCTAGAACACA  3601
AAAAAAAAAAAAAAAAAAAAAAAAAAAAAAAAA                             3693
```

DNA CLONE OF HUMAN THROMBOMODULIN AND PORTIONS THEREOF

BACKGROUND OF THE INVENTION

This invention relates to human thrombomodulin and, more particularly, to the cDNA clone representing the full size human thrombomodulin.

Thrombomodulin is an endothelial cell surface thrombin-binding glycoprotein which converts thrombin into a protein C activator. Activated protein C then functions as an anticoagulant by inactivating two regulatory proteins of the clotting system, namely factors Va and VIIIa. The latter two proteins are essential for the function of two of the coagulation proteases, namely factors IXa and Xa. Thrombomodulin thus plays an active role in blood clot formation in vivo and can function as a direct or indirect anticoagulant.

Thrombomodulin has been purified from rabbit [Esmon et al., *J. Biol. Chem.* 257, 859–864 (1982)], bovine [Suzuki et al., *Biochim. Biophys. Acta* 882, 343–352 (1986); Jakubowski et al., *J. Biol. Chem.* 261, 3876–3882 (1986)], human lung [Maruyama et al., *J. Clin. Invest.* 75, 987–991 (1985)] and human placenta [Salem et al., *J. Biol. Chem.* 259, 12246–12251 (1984)]. The human protein has an apparent $M_r=75,000$ (unreduced) that exhibits a characteristic shift to $M_r=100,000$ upon reduction with 2-mercaptoethanol. Immunohistochemical examination of tissue sections revealed that thrombomodulin is widely distributed in the endothelium of arteries, veins, capillaries, and lymphatics [Maruyama et al., J. Cell Biol. 101, 363–371 (1985)].

Recent advances in biochemistry and in recombinant DNA technology have made it possible to synthesize specific proteins, for example, enzymes, under controlled conditions independent of the organism from which they are normally isolated. These biochemical synthetic methods employ enzymes and subcellular components of the protein synthesizing systems of living cells, either in vitro in cell-free systems, or in vivo in microorganisms. In either case, the principal element is provision of a deoxyribonucleic acid (DNA) of specific sequence which contains the information required to specify the desired amino acid sequence. Such a specific DNA sequence is termed a gene. The coding relationships whereby a deoxyribonucleotide sequence is used to specify the amino acid sequence of a protein is well-known and operates according to a fundamental set of principles. See, for example, Watson, *Molecular Biology of the Gene*, 3d ed., Benjamin-Cummings, Menlo Park, Calif., 1976.

A cloned gene may be used to specify the amino acid sequence of proteins synthesized by in vitro systems. RNA-directed protein synthesizing systems are well-established in the art. Double-stranded DNA can be induced to generate messenger RNA (mRNA) in vitro with subsequent high fidelity translation of the RNA sequence into protein.

It is now possible to isolate specific genes or portions thereof from higher organisms, such as man and animals, and to transfer the genes or fragments to microorganisms such as bacteria or yeasts. The transferred gene is replicated and propogated as the transformed microorganism replicates. Consequently, the transformed microorganism is endowed with the capacity to make the desired protein or gene which it encodes, for example, an enzyme, and then passes on this capability to its progeny. See, for example, Cohen and Boyer, U.S. Pat. Nos. 4,237,224 and 4,468,464.

BRIEF DESCRIPTION OF THE INVENTION

In accordance with the present invention, the complete coding sequence of the cDNA clone representing the full size human thrombomodulin has been developed. The clone, λHTm15, contains a 3693 base pair (bp) cDNA insert with an apparent 5'-noncoding region of 146 bp, an open reading frame of 1725 bp, a stop codon, a 3'-noncoding region of 1779 bp, and a poly(A) tail of 40 bp.

The cDNA sequence encodes a 60.3 kDA ($M_r=60,328$) protein of 575 amino acids. This protein sequence includes a signal peptide of ~21 amino acids, an amino-terminal ligand-binding domain of ~223 amino acids, an epidermal growth factor (EGF)-homology region of 236 amino acids, a serine/threonine-rich segment of 34 amino acids, a membrane-spanning domain of 23 amino acids, and a cytoplasmic tail of 38 amino acids.

The EGF-homology region consists of six tandemly repeated EGF-like domains. The organization of thrombomodulin is similar to that of the low density lipoprotein (LDL) receptor, and the protein is homologous to a large number of other proteins that also contain EGF-like domains, including factor VII, factor IX, factor X, factor XII, protein C, tissue plasminogen activator and urokinase. Homology between amino acid sequences of protein segments encoded by the LDL receptor gene and several proteins of the blood clotting system has been described heretofore by Südhof et al., *Science* 228, 815–822(1985).

There are five potential N-glycosylation sites in the thrombomodulin protein with the sequence Asn-X-Ser/Thr, wherein X can be any of the common 20 amino acids. These sites are at amino acid positions Asn 47, Asn 115, Asn 116, Asn 382 and Asn 409. Glycosylation may also occur in the serine/threonine-rich segment that contains 8 hydroxyamino acids among its 34 residues. These OH sites may be glycosylated with O-linked carbohydrate chains as in the corresponding domain of the LDL receptor [Russell et al., *Cell* 37, 577–585 (1984)].

The original source of the genetic material for developing the thrombomodulin cDNA was human umbilical vein endothelial cells. Such cells are widely available from human tissue sources after delivery by conventional surgical procedures. The primary tissue can be cultured essentially by established methodology such as described by Jaffe et al., *J. Clin. Invest.* 52, 2745–2756 (1973), and Jaffe, *Transplantation Proc.* 12(3), Supp. 1, 49–53 (1980).

In brief, a human umbilical vein endothelial cell cDNA library in the expression vector, λgt11, was screened with affinity-purified rabbit polyclonal anti-human thrombomodulin IgG. Among 7 million independent recombinants screened, 12 positives expressed a protein recognized both by this polyclonal antibody and also by a mouse monoclonal antibody to human thrombomodulin IgG. The λgt11 (lac5 nin5 c1857 S100) used herein is a well-known and commonly available lambda phage expression vector. Its construction and restriction endonuclease map is described by Young and Davis, *Proc. Natl. Acad. Sci. USA* 80, 1194–1198 (1983). Its use in the screening of human placenta and endothelial cell cDNA libraries is described by Ye et al., *J. Biol. Chem.* 262, 3718–3725 (1987).

Thrombomodulin was purified to homogeneity from human placenta, and tryptic peptides were isolated and sequenced using a gas-phase sequencer. The sequence obtained from one peptide,

ANCEYQCQPLNQTSYLCVCAEGFAP, exactly matched that predicted from the cDNA sequence of the isolate, λHTm15, confirming that it encoded human thrombomodulin. Northern blotting with this cDNA insert as the probe identified a single ~3.7 kb mRNA species in human placenta and endothelial cell poly(A)+ RNA.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention in conjunction with the appended drawings, in which briefly:

FIG. 1 is a graphical representation which shows the chromatographic elution profiles obtained from total tryptic digests of reduced, alkylated thrombomodulin. Panel (a) shows the resolution by reverse phase high performance liquid chromatography (HPLC); Panel (b) shows the resolution by anion exchange chromatography; and Panel (c) shows the resolution of one pool from Panel (b) resolved by reversed phase HPLC.

FIG. 3 shows the nucleotide sequence of the human thrombomodulin cDNA and the amino acid sequence of the thrombomodulin protein. The 3693 bp cDNA of clone λHTm15 of FIG. 2 is split into Panels A through F of FIG. 3.

FIG. 4 shows the amino acid sequences of six tandemly repeated EGF-like domains in the thrombomodulin of FIG. 3.

Figure 1:
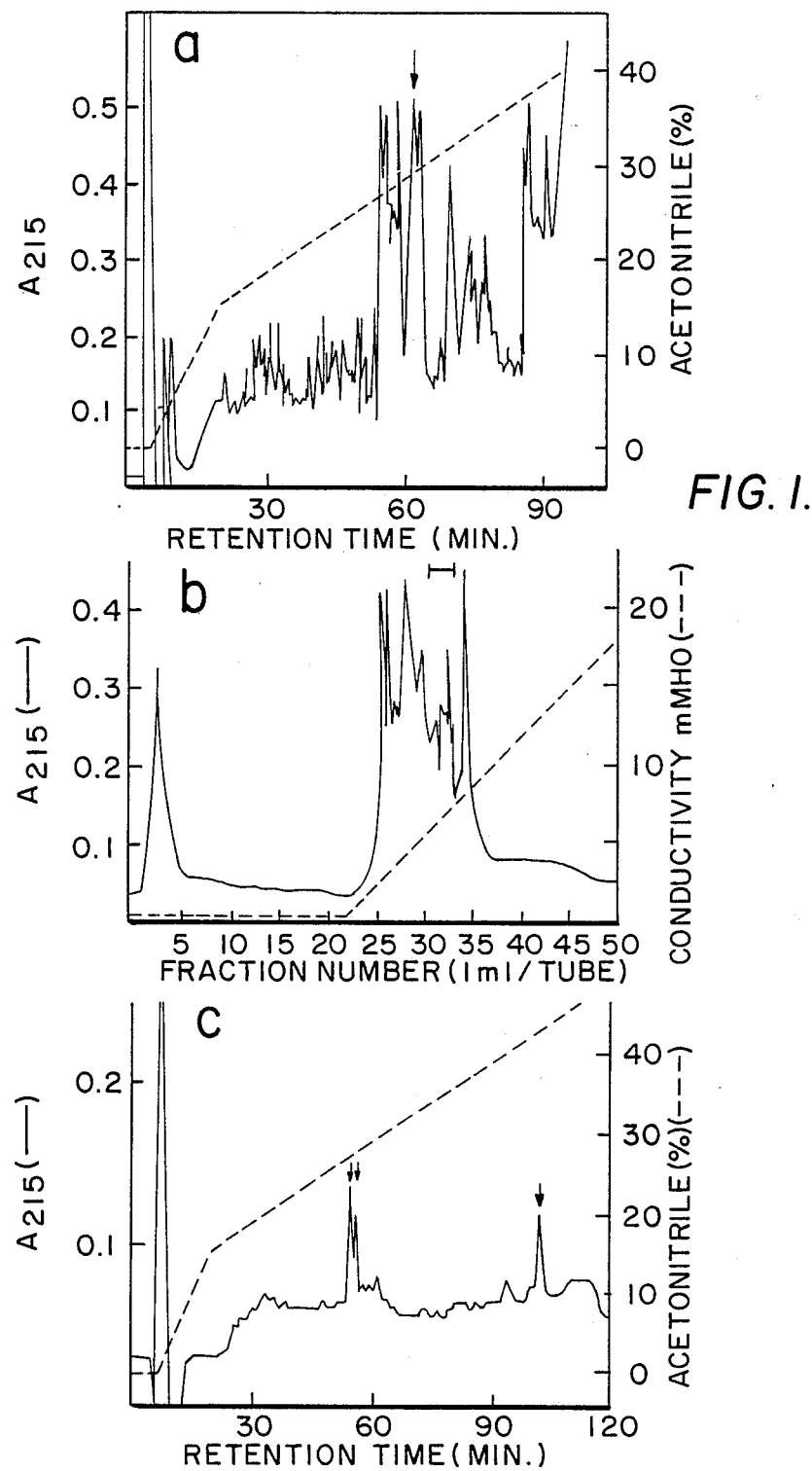

Standard biochemical nomenclature is used herein in which the nucleotide bases are designated as adenine (A); thymine (T); guanine (G); and cytosine (C). Corresponding nucleotides are, for example, deoxyguanosine-5'-triphosphate (dGTP). Amino acids are shown either by three letter or one letter abbreviations as follows:

| Abbreviated Designation | Amino Acid |
| --- | --- |
| A Ala | Alanine |
| C Cys | Cysteine |
| D Asp | Aspartic acid |
| E Glu | Glutamic acid |
| F Phe | Phenylalanine |
| G Gly | Glycine |
| H His | Histidine |
| I Ile | Isoleucine |
| K Lys | Lysine |
| L Leu | Leucine |
| M Met | Methionine |
| N Asn | Asparagine |

| Abbreviated Designation | Amino Acid |
| --- | --- |
| P Pro | Proline |
| Q Gln | Glutamine |
| R Arg | Arginine |
| S Ser | Serine |
| T Thr | Threonine |
| V Val | Valine |
| W Trp | Tryptophan |
| Y Tyr | Tyrosine |

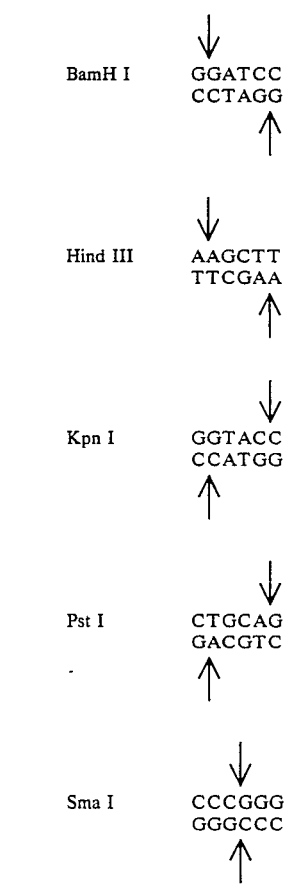

In order to illustrate specific preferred embodiments of the invention in greater detail, the following exemplary laboratory preparative work was carried out.

EXAMPLE

Materials—Deoxy-7-deazaguanosine 5'-triphosate was obtained from Boehringer Mannheim. $^{32}$P-labeled deoxyribonucleotides and deoxyadenosine 5'-[α-$^{35}$S]thiotriphosate were obtained from Amersham Radiochemicals. TPCK-trypsin was obtained from Cooper Biomedical, Malvern, PA. Goat anti-rabbit IgG and goat anti-mouse IgG conjugated with alkaline phosphatase were obtained from Promega Biotec. RNA size standards were obtained from Bethesda Research Laboratories.

Antibodies to Human Thrombomodulin—A monoclonal antibody to human thrombomodulin was isolated as previously described by Maruyama and Majerus, J. Biol. Chem. 260, 15432–15438 (1985). Polyclonal antibodies were prepared by injecting 50 μg of human thrombomodulin into each of two male rabbits by the method of Vaitukaitus, *Methods Enzymol.* 73, 46–52 (1981). Serum and purified IgG were prepared and assayed for inhibition of thrombomodulin functional activity as described by Salem et al, *J. Biol. Chem.* 259, 12246–12251 (1984). Polyclonal IgG was affinity purified by application of 2.3 mg of purified IgG onto a thrombomodulin-Affigel-15 column (165 µg thrombomodulin/4 ml Affigel-15) equilibrated with 50mM N-2-hydroxyethylpiperazine-N'-2-ethanesulfonic acid (HEPES), pH 7.5, 150 mM NaCl. After washing with the same buffer, bound IgG was eluted with 200 mM glycine, pH 3.0, and immediately dialyzed against 50 mM HEPES, pH 7.5, 500 mM NaCl. The yield of antibody was 35 µg.

Preparation of Tryptic Peptides of Thrombomodulin—Human thrombomodulin was purified as previously described by Salem et al., supra, except that immunoaffinity chromatography on polyclonal anti-thrombomodulin IgG-Affigel-10 was substituted for ion exchange chromatography [Ishii and Majerus, *J. Clin. Invest.* 76, 2178–2181(1985)]. Thrombomodulin (1.0-1.3 mg) was concentrated by ultrafiltration in a Micro-ProDiCon (Bio-Molecular Dynamics, Beaverton, Oreg.) to 1 mg/ml and precipitated at $-20°$ in 90% acetone. The precipitate was dried under a stream of nitrogen and redissolved in 0.4M Tris-HCl, 0.1 (w/v) sodium dodecyl sulfate, pH 8.8. 2-Mercaptoethanol was added to 0.15M, and the sample was incubated at 37° for 30 minutes. Iodoacetamide was added to 0.25M and the sample was incubated in the dark at 25° for 3 minutes, then 2-mercaptoethanol was added to 0.3M. The sample was again precipitated at $-20°$ with 90% acetone and dried under nitrogen, then redissolved in 0.5M ammonium bicarbonate, pH 8.5. Alternatively, in a different preparation after the initial precipitation, thrombomodulin was redissolved in 6 M guanidine, 0.5M Tris-HCl, pH 8.8, and a 5-fold molar excess of dithiothreitol over cystine was added, followed by incubation under nitrogen at 50° for 30 minutes. The pH was adjusted to 8.0 with HCl, a 5-fold molar excess of iodoacetamide was added and the sample was incubated at 25° for 40 minutes. Excess iodoacetamide was reacted with a 3-fold molar excess of 2-mercaptoethanol, and the sample was dialyzed against 0.5 ammonium bicarbonate, pH 8.5. N-Tosyl-L-phenylalanine chloromethylketone (TPCK)-trypsin was added (1/100, w/w) and samples were incubated at 37° for 24 hours, then lyophilized. The tryptic peptides were applied either directly to a reverse phase HPLC column, or first to a Mono-Q anion exchange column (5×50 mm, Pharmacia) followed by a reverse phase HPLC column. The Mono-Q column was equilibrated on a Varian 5000 HPLC system in 20 mM Tris-HCl, pH 9.0, and eluted with a linear 0 to 1M NaCl gradient at 1 ml/min over 60 min. The effluent was monitored for absorbance at 215 nm. Fractions were pooled and lyophylized as indicated in the detailed description of FIG. 1, below.

Samples were applied to a reverse phase HPLC column (Unimetrics-Knauer, Licosorb RP-8, 5 µm) equilibrated with 0.1% trifluoroacetic acid, and eluted with a gradient of 0 to 15% (v/v) acetonitrile in 0.1% trifluoroacetic acid over 10 minutes, then to 40% (v/v) acetonitrile, 0.1% trifluoroacetic acid over 75 min. at 0.7 ml/min. The effluent was monitored for absorbance at 215 nm. Individual peaks were pooled and evaporated to near dryness under a stream of nitrogen and sequenced using an Applied Biosystems model 470A gas phase protein sequencer [Hunkapiller et al, *Methods Enzymol.* 91, 399–413 (1983); Hunkapiller and Hood, *Ibid.*, 486–493].

Isolation of cDNA Clones for Human Thrombomodulin—The human umbilical vein endothelial cDNA library in λgt11, procedures for screening cDNA libraries with antibodies, preparation and use of synthetic oligonucleotides and cDNA restriction fragment probes, plaque purification of λ-phage, and preparation of λ-phage DNA were as described previously by Ye et al., *J Biol. Chem.* 262, 3718–3725 (1987), with the exception that the goat anti-rabbit or goat anti-mouse detecting antibody was conjugated with alkaline phosphatase [Blake et al, Anal. *Biochem.* 136, 175–179 (1984)]. The affinity-purified rabbit anti-human thrombomodulin was used at a concentration of 0.1 µg/ml. The monoclonal mouse anti-human thrombomodulin was used at a concentration of 2 µg/ml.

DNA Sequence Analysis—DNA restriction fragments were subcloned into the well-known and commonly available vectors pUC18, pUC19, M13mp18, or M13mp19 as described previously by Ye et al, supra. Nucleotide sequence was determined on both strands by the dideoxy method of Sanger, et al, *Proc. Nat'l. Acad. Sci. USA* 74, 5463–5467 (1977), using deoxyadenosine 5'-[α-$^{35}$S]thiotriphosphate and buffer-gradient gels [Biggin et al, *Ibid.*, 80, 3963–3965 (1983)]. Deletions were generated using exonuclease III [Henikoff, *Gene-(Amst.)* 28, 351–359 (1984)]. Remaining gaps were filled by sequencing with synthetic oligonucleotide primers. Deoxyguanosine 5'-triphosphate (dGTP) in the sequencing reaction was substituted by deoxy-7-deazaguanosine 5'-triphosphate to increase the accuracy of sequencing in G-C rich regions [Mizusawa et al, *Nucleic Acids Res.* 14, 1319–1324 (1986)]. The few persistent compressions were resolved by performing electrophoresis on 6% (w/v) acrylamide gels containing 7M urea and 40% (v/v) formamide.

Northern Blot Analysis-Poly(A)+ RNA was prepared from human term placenta, human umbilical vein endothelial cells, HepG2 cells and also from U937 cells cultured in the presence or absence of phorbol 12-myristate 13-acetate as previously described by Ye et al, supra. RNA was prepared from human brain. Electrophoresis through agarose in the presence of formaldehyde, transfer to nitrocellulose and hybridization was performed as described previously by Ye et al, supra. For each source that did not yield a hybridization signal for human thrombomodulin, control hybridization with either human γ-actin [Gunning et al, *Mol. Cell Biol.* 3, 787–795 (1983)]or human tissue factor cDNA [Scarpati el al, *Fed. Proc.*, in press (1987)]confirmed that RNA had been transferred efficiently.

Chromosome Looalization of the Human Thrombomodulin Gene—Human chromosome suspensions were prepared by the procedure of Sillar and Young, *J. Hist. Cytochem.* 29, 74 (1981), stained with the commonly available chromophores Hoechst 33258 and chromomycin A3, sorted using a dual-laser flow cytometer, hybridized to cDNA probes, and signals were detected by methodology as previously described by Murray et al., *Biochem. Biophys Res. Commun.* 142(1), 141–146 (1987). See also Bartholdi et al, *Methods Enzymol.*, in press (1987). The cDNA insert of λHTm10 was labeled with Klenow fragment (DNA Polymerase I, large fragment) [Feinberg and Vogelstein, *Anal. Biochem.* 132, 6–10 (1983)] to a specific activity of $\geq 10^9$ cpm/µg. Two complete filter sets of the 22 autosomes and both sex chromosomes were examined, as well as Southern blots of human genomic DNA digested with EcoRI [Chomczynski and Qasba, *Biochem. Biophys. Res. Commun.* 122, 340–344 (1984)].

*Computer Analysis of Sequences*—The human thrombomodulin protein sequence was compared to all entries in the NBRF Protein Sequence Database (Georgetown University, Washington, D.C., release 11.0, Dec. 4, 1986) with the computer programs SEARCH [Dayhoff et al, *Methods Enzymol.* 91, 524–545 (1983)] and FASTP [Lipman and Pearson, Science 227, 1435–1441 (1985)]. The nucleotide sequence of cDNA isolate λHTm15 was compared to all entries in the Genbank genetic sequence data bank (BBN Laboratories Inc., Cambridge, Mass. release 48.0, Feb. 16, 1987) with the program FASTN (Lipman and Pearson, supra.) The alignment of EGF-like domains in thrombomodulin and other proteins, including a partial sequence of bovine thrombomodulin [Jackman et al, *Proc. Natl. Acad. Sci. USA* 83, 8834–8838d (1986)] was performed with the programs RELATE and ALIGN (Dayhoff et al, supra.) Nucleotide sequences of human and bovine thrombomodulin were aligned using the program NUCALN Wilbur and Lipman, *Proc. Natl. Acad. Sci. USA* 80, 726–730 (1983)]. Hydropathy or hydrophilicity profiles of the human thrombomodulin precursor were computed by the methods of Hopp and Woods, *Proc. Natl. Acad. Sci. USA* 78, 3824–3828 (1981) and Kyte and Doolittle, *J. Mol. Biol.* 157, 105–132 (1982).

The results of the above laboratory preparative work leading to the complete coding sequence of the cDNA clone representing the full size human thrombomodulin are further exemplified by the following detailed description of FIGS. 1 to 7 of the drawings.

FIG. 1

FIG. 1 shows the separation of tryptic peptides of thrombomodulin in three Panels - a, b and c, as follows: (a) A total tryptic digest of reduced, alkylated thrombomodulin was prepared and chromatographed as described above on a Licosorb RP-8 column. 700 μg of protein was injected and 1 min (0.7 ml) fractions were collected. The solid line ——— indicates absorbance at 215 nm and the dashed line(– – –) indicates the percent acetonitrile in the column buffer. The peak marked with the arrow ( ↓ ) corresponds to peptide T-R1. (b) A total typtic digest of thrombomodulin wa prepared and chromatographed on a Mono-Q column as described above. After injection of 700 μg of protein, 1 ml fractions were collected. The solid line (——) indicates absorbance at 215 nm and the dashedline (– – –) indicates conductivity of the column buffer. The limit buffer had a conductivity of 41 mmho. The fractions indicated by the bar were pooled (T-M1) for further purification on a reversed phase column as shown in Panel c. (c) Pooled sample T-M1 from Panel b was chromatographed on a Licosorb RP-8 column as in Panel a. The doublet eluting at approximately 55 minutes yielded peptides T-M1-R1 and T-M1-R and the single peak at approximately 102 minutes yielded T-M1-R3.

FIG. 1 thus shows the results of the preparation and sequencing of tryptic peptides of human thrombomodulin whereby thrombomodulin was purified to homogeneity from human placenta, reduced and carboxyamidomethylated, and digested with bovine trypsin. The resultant complex mixture of peptides was resolved by reverse phase HPLC (Panel a), yielding peptide T-R1. Subsequent tryptic digests were first separated by anion exchange chromatography, and pools of the individual peaks were further resolved by reverse phase chromatography. For example, pool T-M1 from a Mono-Q column (Panel b), yielded homogeneous peptides T-M1-R1, T-M1-R2, and T-M1-R3 after reversed phase chromatography (Panel c). One other peptide was isolated using similar methods as described above. The partial sequences of five peptides containing a total of 62 amino acid residues were determined.

FIG. 2

Figure 2:
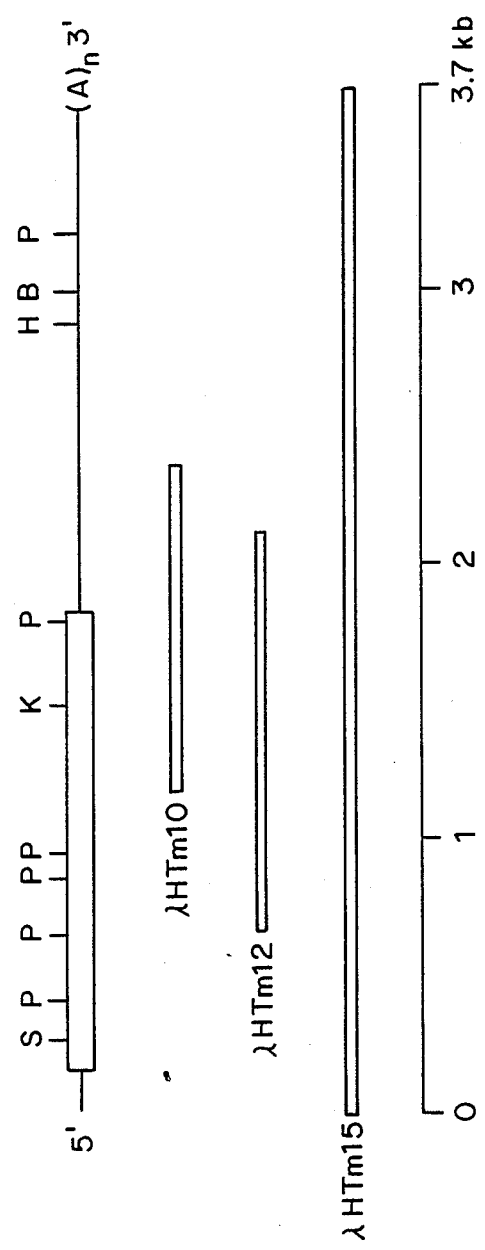
FIG. 2 shows the restriction enzyme map of the full thrombomodulin cDNA clone λHTm15 and two other isolates representing partial thrombomodulin cDNA sequences, λHTm10 and λHTm12.

FIG. 2 shows the restriction map of thrombomodulin cDNA isolates. The 5' and 3' ends of the restriction map are labeled. Selected restriction sites that were useful in subcloning the cDNA inserts for sequencing are shown: BamHI, B; HindIII, H; KpnI, K; PstI, P; SmaI, S. The thin segments indicates noncoding sequences and the thick segment indicates the open reading frame that encodes thrombomodulin. The portion of the sequence contained in each of the cDNA isolates, λHTm10, λHTm12, and λHTm15, is shown by the thin open bars. The scale is in kilobases (kb).

FIG. 2 thus shows the results of the screening of an endothelial cell λgt11 cDNA library and characterization of recombinant proteins whereby the cDNA library was screened with affinity-purified rabbit anti-human thrombomodulin IgG. Among $7 \times 10^6$ independent recombinant clones screened, 12 expressed a fusion protein recognized both by the polyclonal antibody and also by a monoclonal antibody to human thrombomodulin. The cDNA inserts of the twelve isolates were subcloned into pUC19 for further characterization. The length of the inserts ranged from 1.2 kb to 1.7 kb. Although all twelve isolates were initially selected by the same polyclonal and monoclonal antibodies, by cross-hybridization they fell into three unrelated groups of one, two, or nine members. Representatives of each group were sequenced for comparison with independently determined protein sequence. The 5'-sequence of one isolate from the two member group, λHTm10, exactly encoded the sequence of peptide T-R1. Similarly, the 5'-sequence of the second member of this hybridization group, λHTm12, encoded peptides T-M1-R1 and T-MO-R1, and the 3'-sequences of both isolates overlapped, confirming that they encoded human thrombomodulin.

The cDNA insert of clone λHTm10 was used to screen $1 \times 10^6$ recombinants from the endothelial cell cDNA library by plaque hybridization. Ninety positive clones were detected and half of these were plaque purified. The forty-five clones were then rescreened with an oligonucleotide probe corresponding to the 5'-end of clone λHTm12. Nine positive clones were detected, and among them four clones contained a poly(A) tail as determined by hybridization to an oligo(dT) probe. Restriction analysis showed that of these four clones λHTm15 contained the largest cDNA insert of 3.7 kb. The relationship of the three cDNA isolates, λHTm10, HTm12, and λHTm15, to the restriction map of the full-length thrombomodulin cDNA is shown in FIG. 2.

FIG. 3

FIG. 3 shows the nucleotide and translated amino acid sequence of human thrombomodulin cDNA isolate λHTm15. Nucleotides and amino acids are numbered on the right. Nucleotide 1 was assigned to the first residue of the cDNA insert, and amino acid 1 was assigned to the first methionine of the open reading frame that encodes thrombomodulin peptide sequences. Potential N-linked glycosylation sites are marked by filled circles (●). Sequences that match that determined for tryptic peptides of thrombomodulin are marked by bold overlining. The six EGF-like repeats are underlined and numbered. Potential polyadenylation or processing signals AATAAA are marked with bold underlining. The sequence represented in λHTm10 includes nucleotides 1208-2403, and λHTm12 includes nucleotides 671-2142.

Nucleotide Sequence of Thrombomodulin cDNA Isolates—The cDNA insert of λHTm12 (1.5 kb) was sequenced completely on both strands. The cDNA insert of λHTm15 (3.7 kb) was sequenced on at least one strand, and those regions at the 5' and 3' ends that did not overlap with λHTm12 were sequenced on both strands. Thus, the complete sequence was determined at least once on both strands. The coding sequence of thrombomodulin has an extremely high G+C content of 68% that made sequencing difficult due to frequent compressions. All of these were resolved by the use of deoxy-7-deazaguanosine 5'-triphosphate in place of dGTP except for a short sequence between nucleotides 395-405. This sequence was resolved unambiguously on both strands by the use of sequencing gels containing 40% (v/v) formamide in addition to urea. In contrast to the high G+C content of the coding sequence, the 3'-noncoding sequence is only ~43% G+C.

The nucleotide and translated amino acid sequence of λHTm15 is shown in FIG. 3. The first ATG codon occurs at nucleotide 147, embedded in a sequence that agrees well with the proposed optimal sequence for initiation by eukaryotic ribosomes, ACCATGG [Kozak, Cell 44, 283-292 (1986)]. The preceding 146 nucleotides of proposed 5'-noncoding sequence does not have a termination codon in the same reading frame as the ATG codon. This proposed initiator codon begins an open reading frame of 1725 nucleotides, followed by TGA termination codon and 1779 additional nucleotides of 3'-noncoding sequence before a poly(A) tail of 40 nucleotides. There are four potential polyadenylation or processing signals with the sequence AATAAA [Proudfoot and Brownlee, Nature 252, 359-362 (1981)], the last of which begins 21 nucleotides before the poly(A) tail.

There is a single nucleotide difference between λHTm12 and λHTm15 at nucleotide 1564, which is a T in λHTm12 and a C in λHTm15. This alters the encoded amino acid sequence from Ala-473 to Val. This could be due to nucleotide sequence polymorphism or the result of an error in DNA replication during cDNA cloning.

FIG. 4

Figure 4:
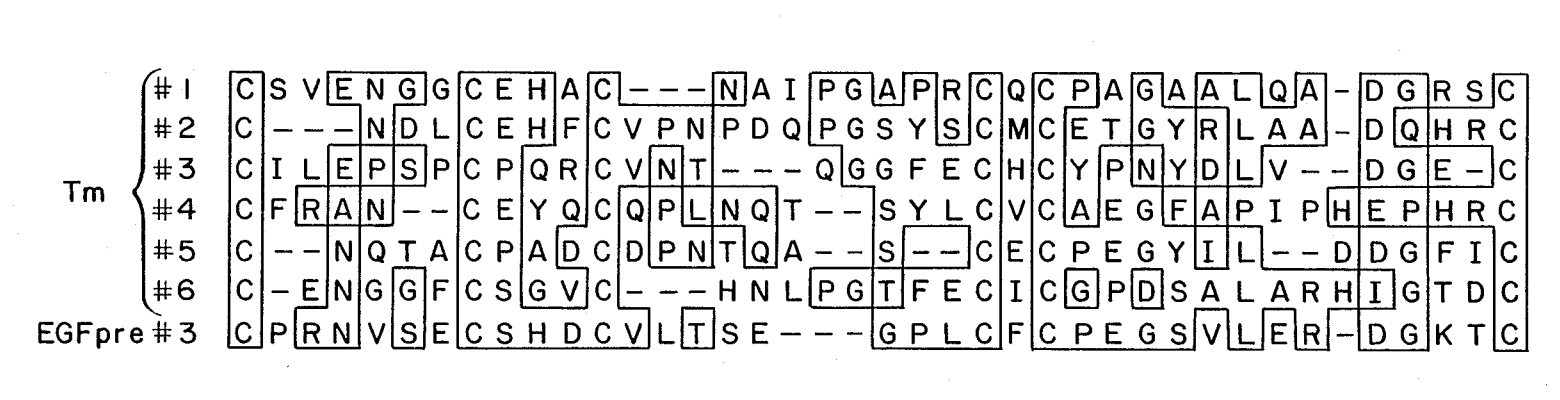

FIG. 4 shows the alignment of the EGF-like repeats of human thrombomodulin. The EGF-like repeats of thrombomodulin are numbered 1-6 as in FIG. 3. The bottom line is the sequence of the third EGF-like domain from the human EGF precursor, residues 401—436 (Bell et al, 1986), a representative sequence for comparison. Dashes (-) represent gaps introduced to optimize the alignment. Residues identical in two or more of the aligned sequences are enclosed in the boxed outlines.

Amino Acid Sequence of Thrombomodulin and Homology to Other Proteins—The cDNA sequence encodes a protein of 575 amino acids with a calculated $M_r = 60,328$. There are five potential N-glycosylation sites with the sequence Asn-X-Ser/Thr (FIG. 3). The amino terminal ~21 residues are hydrophobic with the characteristics of a typical signal peptide [von Heijne, Eur. J. Biochem. 133, 17-21 (1983), J. Mol. Biol. 184, 99-105 (1985)], and the predicted site of cleavage by signal peptidase is between Ala-21 and Glu-22. The remainder of the protein sequence contains the sequence of five tryptic peptides isolated from human placental thrombomodulin (FIG. 3).

The signal peptide is followed by a relatively cysteine-poor domain of ~223 amino acids and a cysteine-rich region of 236 residues composed of six tandem EGF-like repeats of ~40 residues each. The alignment of these EGF repeats with a representative domain from the human EGF precursor [Bell et al, Nucleic Acids Res. 14, 8427-8446 (1986)]is shown in FIG. 4. The amino terminal and EGF-homology regions are followed sequentially by a serine/threonine-rich domain of 34 amino acids, a hydrophobic segment of 23 amino acids that may span the plasma membrane, and a proposed cytoplasmic tail of 38 amino acids.

The amino acid sequence of thrombomodulin was compared to all sequences in the NBRF Protein Sequence Database and the nucleotide sequence of λHTm15 was compared to all entries in the Genbank Genetic Sequence Data Bank, as stated above. Aside from proteins containing EGF-like domains, no protein or DNA sequences showed significant similarity to human thrombomodulin.

FIG. 5

Figures 5, 6:
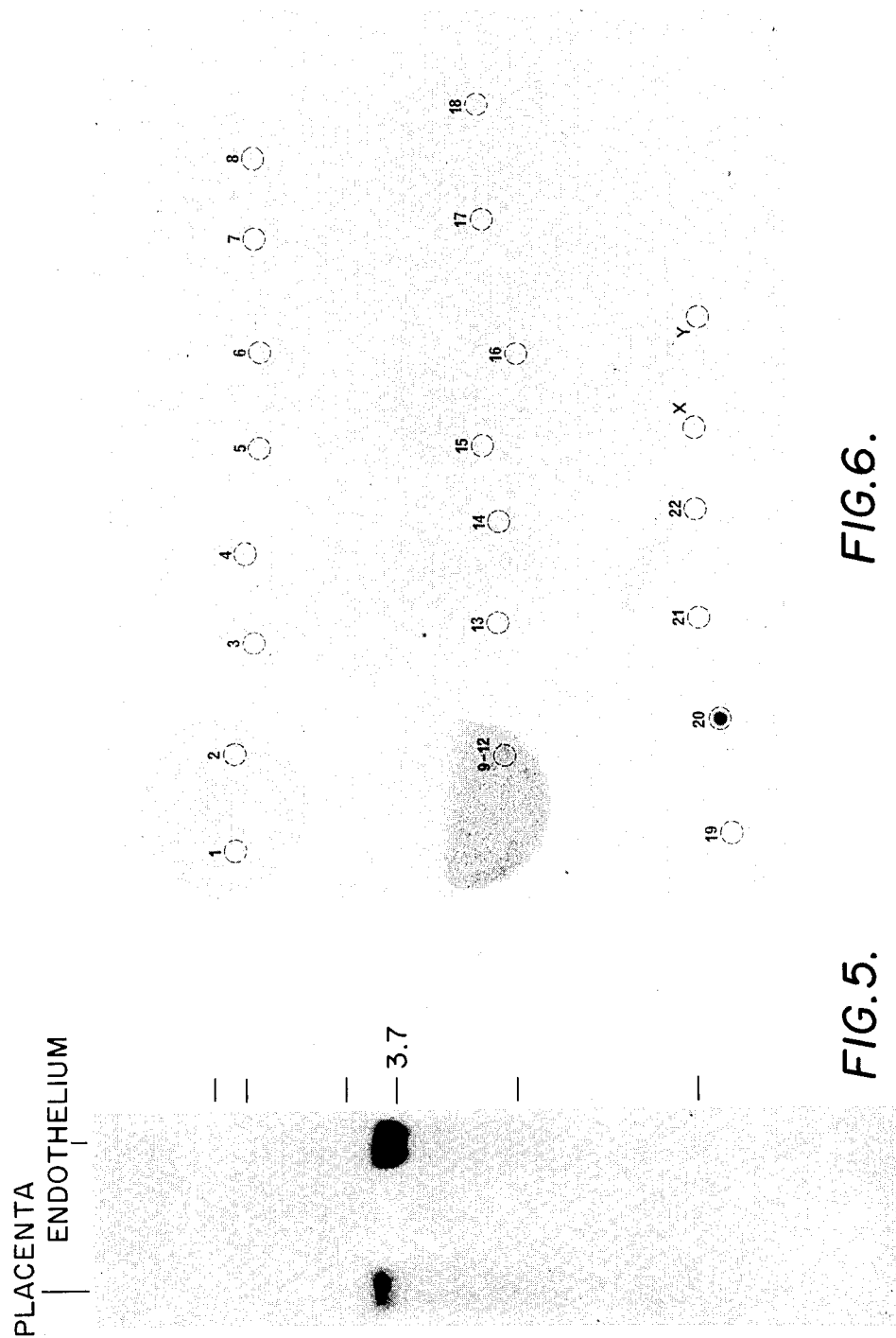
FIG. 5 shows the Northern blot of mRNA from cultured cells probed with the thrombomodulin cDNA insert of λHTm10 of FIG. 2.
FIG. 6 shows the chromosome localization of the human thrombomodulin gene on nitrocellulose filters.
Figure 7:
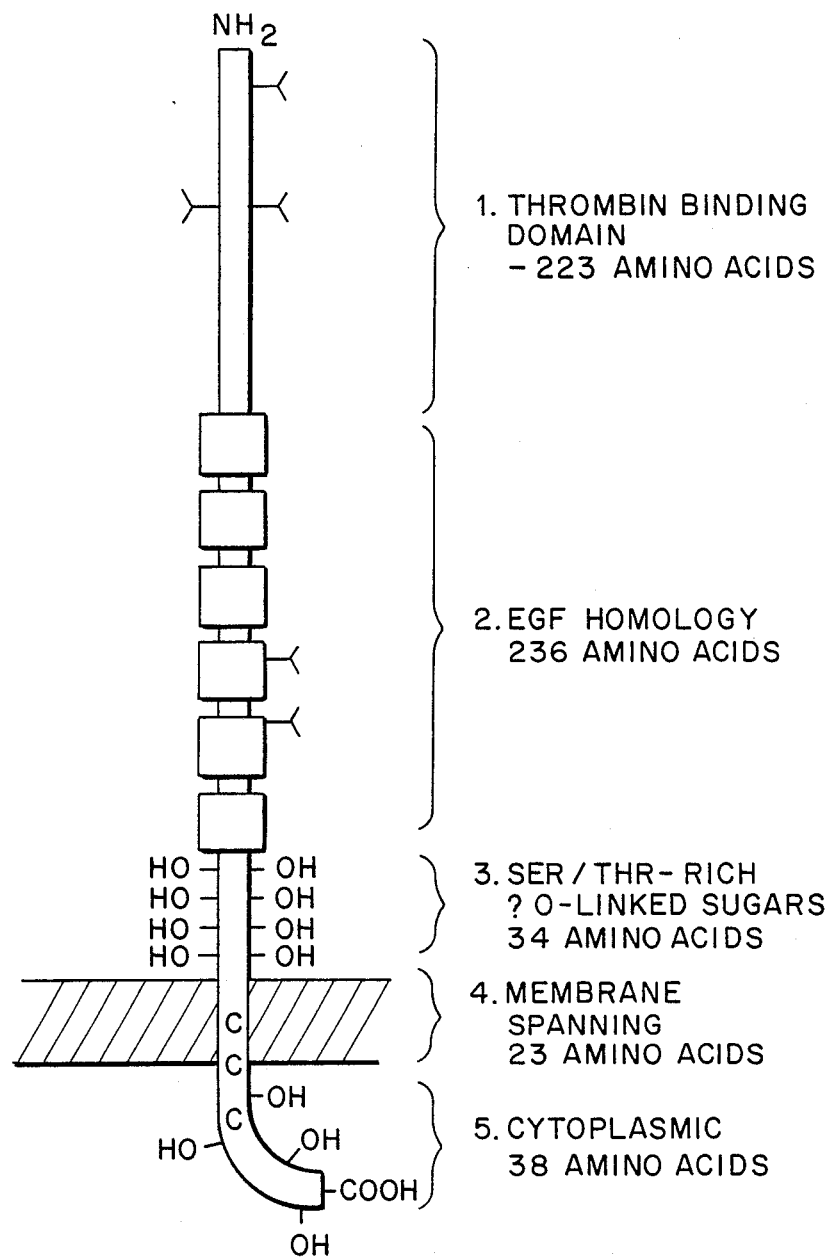
FIG. 7 is a schematic representation which shows the structural domains of human thrombomodulin.

FIG. 5 shows the Northern blot of RNA from cultured cells probed with thrombomodulin cDNA. The cDNA insert of λHTm1O was used to probe a Northern blot as described above. The lanes contain 10 μg (placenta) or 5 μg (endothelium) of poly(A)+ RNA. The position of RNA standards are indicated at the right in descending order: 9.49, 7.46, 4.40, 2.37, and 1.35 kilobases. The interpolated size of thrombomodulin mRNA is 3.7 kilobases.

The Size Occurrence of Thrombomodulin mRNA in Tissues and Cultured Cells—The distribution of mRNA for human thrombomodulin was studied by Northern blotting (FIG. 5). A single mRNA species of 3.7 kb was detected in human placenta and endothelial cell poly(A)+ RNA. Thrombomodulin mRNA was not detected in poly(A)+ RNA from human hepatoma HepG2 cells or the monocytic U937 cell line. In addition, no hybridization was detected with 10 μg of human brain poly(A)+ RNA (data not shown).

FIG. 6

FIG. 6 shows the chromosome localization of the human thrombomodulin gene. The characters 1-22, X and Y, on the nitrocellulose filters indicate the human chromosomes present in each spot that is outlined in the dashed circles.

Chromosome Localization of the Thrombomodulin Gene—The insert of λHTm10 was hybridized to human chromosomes purified by fluorescence-activated flow-sorting. Two complete sets of 22 autosomes and the X and Y chromosomes were tested, both of which gave signals only with chromosome 20 (FIG. 6).

FIG. 7

Figure shows the structural domains of human thrombomodulin. The organization of thrombomodulin is depicted schematically, with the amino-terminus (NH2) and carboxy-terminus (COOH) of the protein labeled. Potential N-glycosylation sites are indicated (Y). Hydroxyamino acids in the serine/threonine-rich domain and the cytoplasmic tail are shown (—OH). Cysteine residues in the transmembrane and cytoplasmic domains are also indicated (C).

The cDNA clone λHTm15 as defined herein can be used for the cloning of the human thrombomodulin DNA in eukaryotic as well as prokaryotic host cells by conventional recombinant DNA technology such as has been used for the synthesis of various other biologically active proteins. See, for example, the brief review by Miller and Baxter, *Drug Devel. Res.* 1, 435–454 (1981). Since the prokaryotic host cells, e.g. *E. coli*, do not usually glycosylate, a variety of novel human thrombomodulin derivatives can be produced by expressing in such host cells. It should also be understood that the invention includes human thrombomodulin from which sequences that are not required for the human thrombomodulin activity have been cleaved, for example, the signal sequences or the N-terminal methionyl.

The thrombomodulin can be used for administration to humans by conventional means, preferably in formulations with pharmaceutically acceptable diluents or carriers. The preferable route of administration is parenteral, especially intravenous. Intravenous administration of the human thrombomodulin in solution with normal physiological saline, human albumin and other such diluents and carriers is illustrative. Other suitable formulations of the active human thrombomodulin in pharmaceutically acceptable diluents and carriers in therapeutic dosage form can be prepared by reference to general texts in the pharmaceutical field such as, for example, *Remington's Pharmaceutical Sciences,* Ed. Arthur Osol, 16th ed., 1980, Mack Publishing Co., Easton, Pa.

Various other examples will be apparent to persons skilled in the art after reading the instant disclosure without departing from the spirit and scope of the invention and it is intended that all such other examples be included within the scope of the appended claims.

What is claimed is:

1. Human thrombomodulin cDNA clone λHTm15 characterized as shown by the restriction map in FIG. 2 of the drawings.

2. The cDNA of human thrombomodulin having the nucleotide sequence as shown in FIG. 3 of the drawings.

3. The partial human thrombomodulin cDNA clone λHTm 10 of 1.2 kb characterized as shown by the restriction map in FIG. 2 of the drawings.

4. The partial human thrombomodulin cDNA having the nucleotide sequence 1208 to 2403 as shown in FIG. 3 of the drawings.

5. The partial human thrombomodulin cDNA clone λHTm12 of 1.5 kb characterized as shown by the restriction map in FIG. 2 of the drawings.

6. The partial human thrombomodulin cDNA having the nucleotide sequence 671 to 2142 as shown in FIG. 3 of the drawings.

* * * * *

UNITED STATES PATENT AND TRADEMARK OFFICE
CERTIFICATE OF CORRECTION

PATENT NO. : 4,912,207

DATED : March 27, 1990

INVENTOR(S) : PHILIP W. MAJERUS and J. EVAN SADLER

It is certified that error appears in the above-identified patent and that said Letters Patent is hereby corrected as shown below:

At col. 4, below the table ending with line 10, the following statements are missing and should be inserted:
"For convenience, certain restriction endonucleases are also indicated by one letter abbreviations in FIG. 2 as follows:

BamH I    =    B
    Hind III    =    H
    Kpn I    =    K
    Pst I    =    P
    Sma I    =    S These are commonly available restriction endonucleases having the following restriction sequences and (indicated by arrows) cleavage patterns:". At col. 5, line 30, "3" should read --30--. At col. 7 line 58, "T-M1-R" should read --T-M1-R2--.

Signed and Sealed this

Twenty-eighth Day of May, 1991

Attest:

HARRY F. MANBECK, JR.

Attesting Officer      Commissioner of Patents and Trademarks